United States Patent [19]

Perusek

[11] Patent Number: 5,093,575
[45] Date of Patent: Mar. 3, 1992

[54] DUAL ROTATABLE HEAD GAMMA CAMERA

[75] Inventor: Allan J. Perusek, Mentor, Ohio

[73] Assignee: Picker International, Inc., Highland Heights, Ohio

[21] Appl. No.: 616,986

[22] Filed: Nov. 21, 1990

[51] Int. Cl.$^5$ .............................................. G01T 1/166
[52] U.S. Cl. ............................ 250/363.08; 250/363.05
[58] Field of Search ....................... 250/363.08, 363.05

[56] References Cited

U.S. PATENT DOCUMENTS

| | | | |
|---|---|---|---|
| 4,220,861 | 9/1980 | Colombo et al. | 250/363.05 |
| 4,368,389 | 1/1983 | Blum | 250/363.05 |
| 4,476,389 | 10/1984 | Ueyama et al. | 250/363.05 |
| 4,928,283 | 5/1990 | Gordon | 378/20 |

OTHER PUBLICATIONS

Triad Spect System; Trionix Research Laboratories, Inc., 1988.
Siemens 7500 Orbiter; MaxDelta DELTAmanager NON W.A.M., W.A.M. advertising brochure; Siemens Medical Systems, Inc.
Nuclear Medicine Instruments and Accessories, Nuclear Associates Division of Victoreen Inc., advertising brochure.
Picker SX-300; Artis 3200 Advertising brochure, Picker International, Inc.
Apex 009; Apex 409ECT; Apex 609 ECT; Apex 409 MA, Apex 209 MA/advertising brochure, Elscint, Inc.
Starcam 3000XG/T; Starcam 3000XR/T; Starcam 2000AG/T advertising brochure, GE Medical Systems.
SPECT Phantom; Data Spectrum Corporation advertising brochure.
Capintec, Inc., CAPTURA System advertising brochure, 1989.
GCA-901A; GCA-602 Digital Gammacamera advertisement; Toshiba Medical Systems.
DS7; DSX advertisement, Sopha Medical Systems, Inc.
Spectrum 1024 DT Digital Imaging System; Spectrum 1024/64 DP Nuclear Data and Image Processor; NeuroSpect 2000 Dedicated Cerebral Imaging System advertisement brochure; Spectrum Medical Systems, Inc.
ECAT advertisement; Siemens Medical Systems, Inc.
ADAC advertisement and design patent application therefor.
SX Series Detector Stands advertisement; Picker International, Inc.
PRISM advertisement; Ohio Imaging, Inc., 1988.
Technology Update; Shimadzu Medical System's Headtome SE T-031, Jun. 1989.

Primary Examiner—Constantine Hannaher
Attorney, Agent, or Firm—Fay, Sharpe, Beall, Fagan, Minnich & McKee

[57] ABSTRACT

A patient is supported along a longitudinal axis for a patient table (10). An outer gantry structure (20) is mounted to move on rails (22) parallel to the longitudinal axis. The outer gantry structure supports a large diameter outer race (46) of a large diameter bearing (42). An inner race (44) of the large diameter bearing doubles as a structural outer frame for an inner gantry structure (30) which defines a patient receiving aperture (36) centrally therethrough. The large diameter bearing enables the inner gantry structure to rotate about the longitudinal axis. A motor (68) selectively adjusts an angular position of a first detector head (32) about a first axis (62) that lies in a plane transverse to the longitudinal axis through the large diameter bearing. A second motor (78) selectively adjusts an angular position of a second detector head (34) about a second axis (72) also lying in the plane. The motors (86) and (96) along with associated drive mechanisms selectively move the first and second camera heads, independently, toward and away from the longitudinal axis.

17 Claims, 4 Drawing Sheets

DUAL ROTATABLE HEAD GAMMA CAMERA

BACKGROUND OF THE INVENTION

The present invention relates to the art of gamma

It finds particular application in conjunction with dual head, rotatable gamma cameras and will be described with particular reference thereto. It is to be appreciated, however, that the invention will also find application in conjunction with single detector head gamma cameras and other medical diagnostic equipment.

Heretofore, gamma cameras have included a relatively large, detector head. In some gamma cameras the head was mounted on an arm or pair of arms to facilitate positioning and moving the head. The arm(s) were mounted for rotating the head about a first axis to enable the head to move along a path encircling the patient. The head was typically mounted pivotally to the pair of arms along an axis transverse to the first axis.

In many models, the arms were centrally pivoted to carry a counterweight for balancing the camera head. Due to the significant volume of lead in the detector head and associated collimators, the counterweights were of significant size. For dual head cameras, a second pair of arms, a second detector head, and a second set of counterweights were provided.

In another prior art camera, the head was mounted on a longitudinally extending beam to traverse back and forth therealong. The beam was mounted at opposite ends to be rotated around the patient while remaining parallel thereto.

In another prior art gamma camera, a pair of stationary circular guide tracks were provided surrounding the patient. The camera head was mounted to the guide tracks to rotate about the longitudinal axis of the patient. Pivotal interconnections were provided such that the head could be rotated about an axis parallel to the longitudinal axis. However, the camera head could not be rotated about axes transverse to the longitudinal axis, limiting its freedom of positioning.

In a prior art three head system, three heads were mounted to a rotatable disk. The heads could move toward and away from the central axis along three, 120° displaced axes, all transverse to the longitudinal axis. However, the heads were not amenable to rotation to face other than parallel to the longitudinal axis.

The present invention contemplates a new and improved gantry assembly that provides more freedom of head positioning.

SUMMARY OF THE INVENTION

In accordance with the present invention, a gamma camera assembly is provided. An inner gantry structure which defines a patient receiving aperture centrally therein along a longitudinal axis is rotatably mounted to an outer gantry structure. A first detector head is mounted to the inner gantry structure. An inner gantry structure rotating means rotates the inner gantry structure around the longitudinal axis. A detector head angular position adjusting means selectively moves the detector head pivotally about a first axis lying in a plane perpendicular to the longitudinal axis. A first head translating means moves the first head closer to or further from the longitudinal axis.

In accordance with another aspect of the invention, a second detector head is mounted to the inner gantry structure. A second head angular position adjusting means selectively adjust the angular position of the second head about a second axis, parallel to the first axis. A second head translating means moves the second head toward and away from the longitudinal axis.

In accordance with another aspect of the present invention, a large diameter bearing is defined between the inner gantry structure and an outer gantry structure. The inner bearing race is at least a part of the inner gantry structure. An inner race of the large diameter bearing is connected with the inner gantry structure and an outer race is connected with the outer gantry structure. In this manner, the large diameter bearing provides for smooth, stable rotation of the inner gantry structure and detector heads around the longitudinal axis.

In accordance with another aspect of the present invention, the means for rotating the inner gantry structure includes a large diameter gear connected with the inner bearing race and a driven gear and a source of motive power for the driven gear operatively connected with the other race. In this manner, the driven and large diameter gear selectively rotate the inner race and camera heads around the longitudinal axis.

In accordance with another aspect of the present invention, a stationary patient table is provided for supporting a patient along the longitudinal axis. Means are provided for moving the outer gantry structure parallel to the longitudinal axis. In this manner, the camera heads are moved longitudinally along the patient, while the patient remains stationary.

One advantage of the present invention is that camera heads are stabily mounted. The oscillations and wavering associated with cantilevered support arms are eliminated.

Another advantage of the present invention is that counterweights are eliminated of a cantilever design. This reduces floor space, improves safety by eliminating impact hazards with moving counterweights, and facilitates the use of collimators with widely varying weights.

Another advantage of the present invention resides in the flexibility of camera head placement. A large variety of symmetric and non-symmetrical camera head positionings are readily selected.

Still further advantages of the present invention will become apparent to those of ordinary skill in the art upon reading and understanding the following detailed description of the preferred embodiments.

BRIEF DESCRIPTION OF THE DRAWINGS

The invention may take for in various parts and arrangements of parts, or in various steps and arrangements of steps. The drawings are only for purposes of illustrating the preferred embodiments and not for purposes of limiting the invention.

Figure 1:
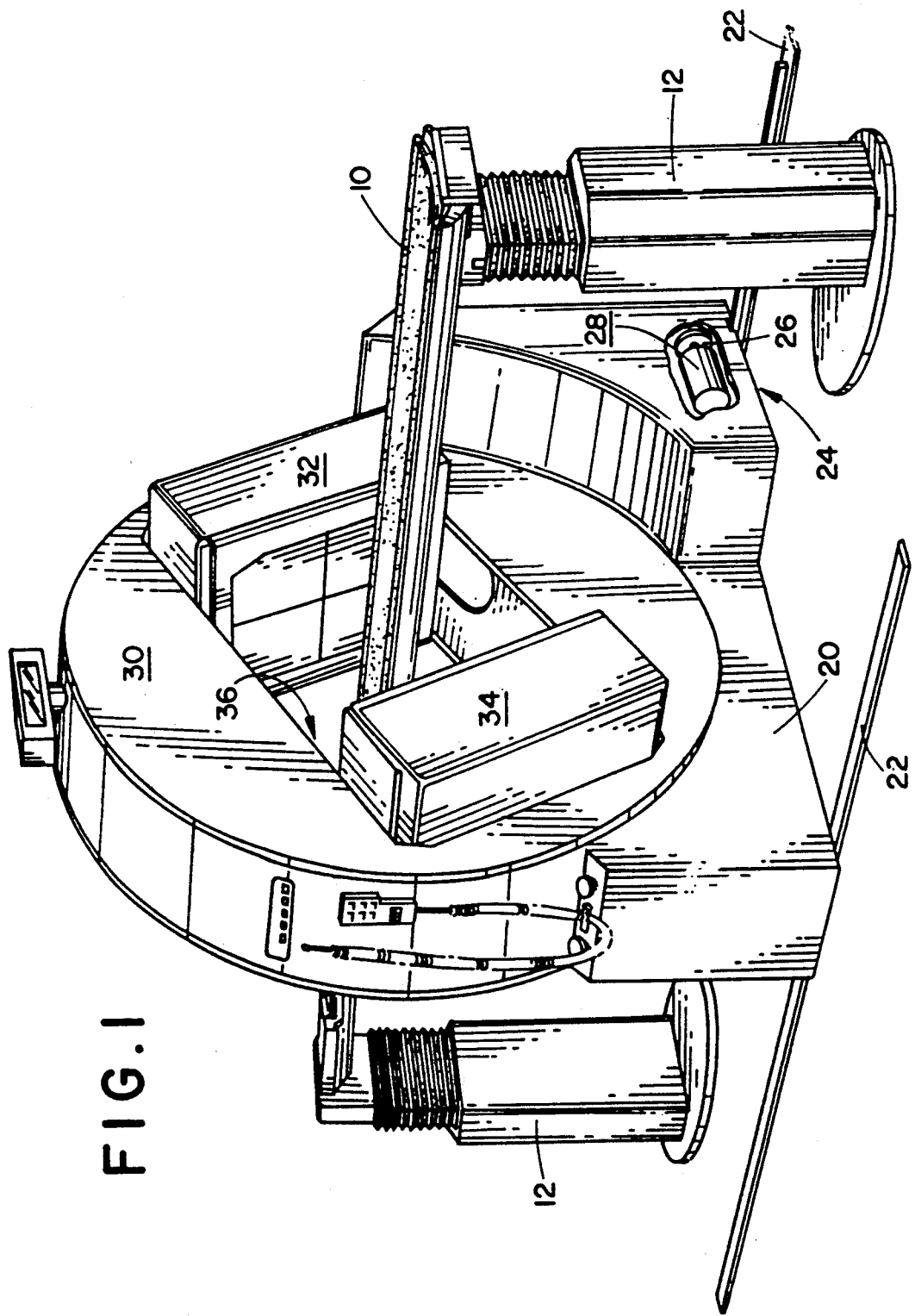
FIG. 1 is a perspective view of a gamma camera assembly in accordance with the present invention.

DETAILED DESCRIPTION OF THE PREFERRED EMBODIMENT,

With reference to FIG. 1, a patient table 10 is mounted to stationary, vertical supports 12 at opposite ends. The patient table is selectively positionable up and down to center the patient in the center of a circle along a longitudinal axis 14, FIG. 4.

An outer gantry structure 20 is movably mounted on tracks 22 which extend parallel to the longitudinal axis. This enables the outer gantry structure to be moved parallel to the longitudinal axis. An outer gantry structure moving means 24 is provided for selectively moving the outer gantry structure 20 along the rails 22 in a path parallel to the longitudinal axis. In the illustrated embodiment, the longitudinal moving means includes wheels 26 for supporting the outer gantry structure on the tracks. A motive power means, such as a motor 28, selectively drives one of the wheels which frictionally engages the track and drives the outer gantry structure and supported inner gantry structure and detector heads therealong.

An inner gantry structure 30 is rotatably mounted on the outer gantry structure 20. A first camera or detector head 32 is movably mounted to the inner gantry structure. A second detector head 34 is movably mounted to the inner gantry structure opposite to the first camera head. The inner gantry structure defines a central, patient receiving aperture 36 for receiving the patient table and, particularly, a supported patient along the longitudinal axis. The aperture 36 is enlarged to receive the detector heads in any of a variety of displacements from the central axis and angular orientations.

The detector heads have collimators on a front face to restrict received radiation to radiation traveling generally perpendicular to the face. The face includes a scintillation crystal that emits a flash of light in response to incident radiation. An array of photomultiplier tables convert the light into electrical signals. A resolver circuit resolves the x, y coordinates of each light flash and the energy of the incident radiation. After appropriate uniformity and linearity correction, the count or number of flashes at each x, y coordinate is converted to gray scale and displayed on a CRT or video monitor.

Figure 2:
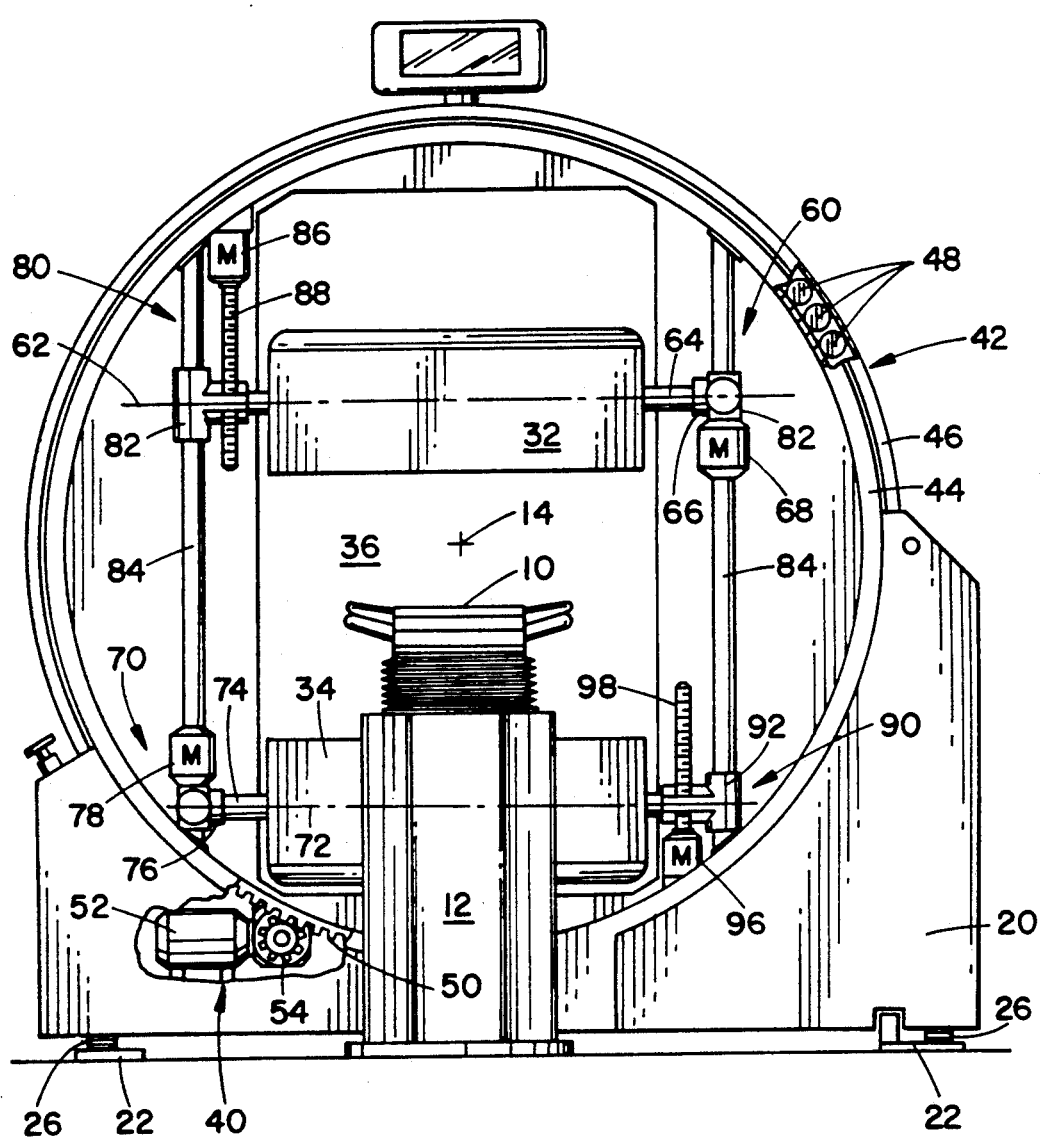
FIG. 2 is a right side view of the camera assembly of FIG. 1 with a side cover of the inner gantry structure removed to illustrate internal structure for rotating the inner gantry structure and for rotating and translating the detector heads.

With reference to FIG. 2, an inner gantry structure rotating means 40 rotates the inner gantry structure 30 relative to the stationary outer gantry structure 20, the inner gantry structure rotating means 40 includes a large diameter bearing 42 having an inner race 44, an outer race 46, a ball or roller bearings 45 therebetween. The inner bearing race 44 extends peripherally around the inner gantry structure 30 and is a main structural member thereof.

A large diameter gear 50 is connected with one of the races, the inner race 44 in the illustrated embodiment. A motive power means such as an electric motor 52 provides rotational energy to a gear 54 that meshes with the large diameter gear 50. By applying motive force with a motor 52 which is mounted to the outer gantry structure, hence the outer race, the inner gantry structure and associated detector heads are caused to rotate around the longitudinal axis relative to the stationary outer gantry structure 20.

A first detector head angular position adjusting means 60 selectively rotates the first detector head 32 about a first axis 62. The first head is mounted to a mounting shaft 64 which is received in bearings 66 to permit the shaft and camera head to rotate around the first axis 62. A motive power means, such as a motor 68 provides motive power through a gear or chain assembly to rotate the mounting shaft 64 hence the detector head.

A second detector head angular position adjusting means 70 rotates the second detector head 34 about the second axis 72. The second head is mounted to a mounting shaft 74 which is received in bearings 76 to permit the shaft and detector head to rotate around the second axis 72. A motive power means, such as a motor 78, provides motive power through a gear or chain assembly to rotate the shaft 74, hence the detector head. The first and second axes are disposed in a plane which is transverse to the longitudinal axis.

A first head translating means 80 selectively moves or translates the first detector head 32 toward and away from the longitudinal axis. The bearings 66 are mounted in slide members 82 which slidably receive sided rods or bars 84 that are secured at opposite ends with the inner race. A motor 86 rotates a drive screw 88 that is threadedly received through one of the slide members 82. By selectively providing energy to the motor 86, the slides 82 on which bearings 64 are mounted are caused to move along rods 84.

A second head traversing means 90 selectively translates or moves the second detector head 34 toward and away from the longitudinal axis. The second head translating means 90 includes slide members 92 in which bearings 76 are mounted. The slide members ride on the rods 84 that are rigidly mounted at opposite ends to the inner race. A motor 96 rotates a drive screw 98 that is threadedly received in one of slide members 92. By selectively providing energy to the motor 96, the slide members 92 are caused to slide along the rods 84 translating shaft 74 and the second detector head parallel to the rods.

With this arrangement, the inner gantry structure rotating means 40 rotates the detector heads continuously or incrementally around the patient. The heads can be positioned stationarily at any angular increment around the longitudinal axis. The first head angular position means 60 adjusts the angular position of the first head 32 about the first axis 62. The second head angular adjustment means 70 rotates and selectively positions the second heat at various angular positions relative to the second axis 72, independently of the position of the first head. The first head translating means 80 and the second head translating means 90 selectively move the first and, second heads, independently, closer to and further from the patient table 10.

Figure 3:
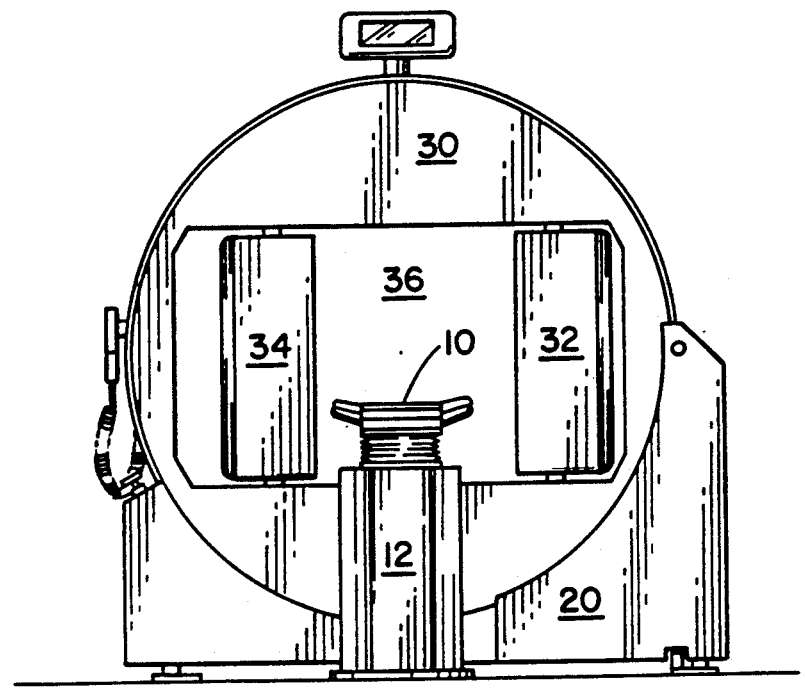
FIG. 3 is a right side view with the inner gantry structure rotated 90° and the detector heads at different radii.
Figure 4:
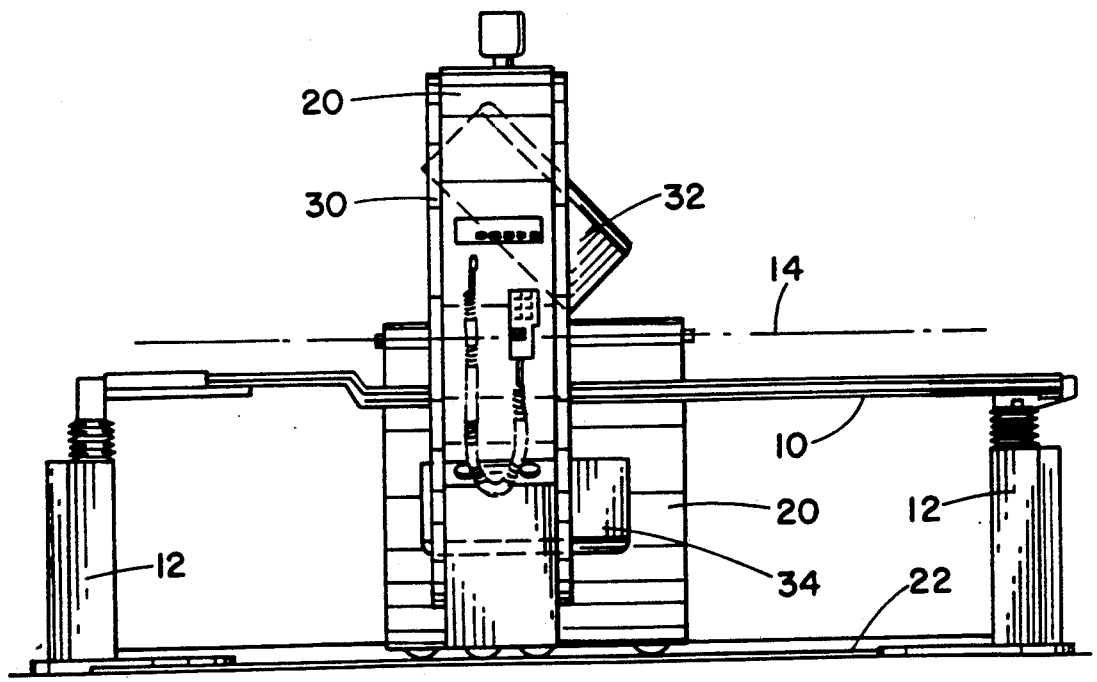
FIG. 4 is a front view with one head at a 45° angle.
Figure 5:
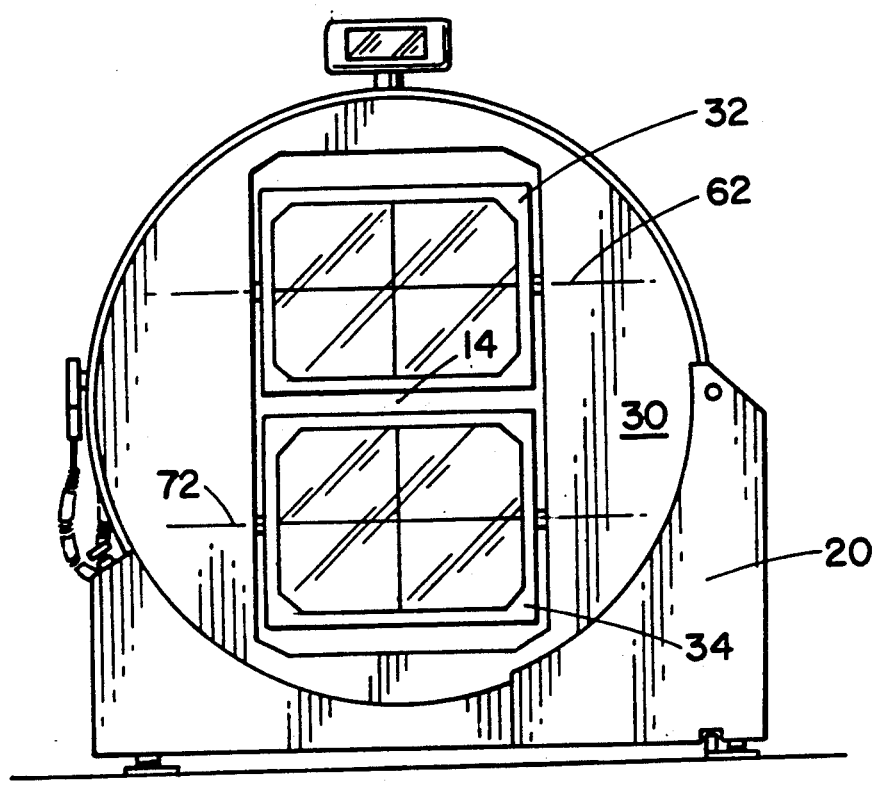
FIG. 5 is a right side view with the patient table removed and both detector heads rotated 90°.

This enables both heads to be positioned facing each other perpendicular to the longitudinal axis and equidistant from the longitudinal axis as illustrated in FIG. 1. The heads can also be positioned different distances from the longitudinal axis, as illustrated in FIG. 3. Analogously, the heads can be adjusted to different angles relative to the longitudinal axis, as illustrated in FIG. 4. The heads can be rotated to where the heads lie in a common plane bother facing parallel to the longitudinal axis, as illustrated in FIG. 5. This position effectively creates a double sized detector head in front of which a patient can stand or sit and be examined concurrently by both heads.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiments, the invention is now claimed to be:

1. A gamma camera assembly comprising:
   an outer gantry structure;
   an inner gantry structure defining a central patient receiving aperture along a longitudinal axis;
   a bearing for rotatably supporting the inner gantry structure in the outer gantry structure for rotation around the longitudinal axis, the bearing defining a bearing plane therethrough which intersects the bearing in a ring of points;
   an inner gantry structure rotating means for selectively rotating the inner gantry structure relative to the outer gantry structure;
   a first detector head;
   a means for mounting the first detector head to the inner gantry structure such that a central portion of the first detector head lies along a first axis which first axis lies in a plane perpendicular to the longitudinal axis and lies within the bearing plane;
   a first detector head angular position adjusting means for selectively rotating the first head around the first axis;
   a first head translating means for selectively translating the first head toward and away from the longitudinal axis with the first detector head central portion translating along the bearing plane.

2. The camera assembly as set forth in claim 1 further including:
   a second detector head mounted to the inner gantry structure;
   a second detector head angular position adjusting means for selectively adjusting an angular position of the second head relative to a second axis parallel to the first axis and lying in the plane perpendicular to the longitudinal axis;
   a second head translating means for selectively translating the second head toward and away from the longitudinal axis.

3. The camera assembly as set forth in claim 2 further including:
   an outer gantry structure moving means for moving the outer gantry structure along the longitudinal axis; and
   a patient supporting table mounted for positioning a supported patient generally along the longitudinal axis.

4. The camera assembly as set forth in claim 3 wherein the bearing includes an inner race connected with the inner gantry structure and an outer race connected with the outer gantry structure, the bearing extending peripherally around the inner gantry structure and the detector heads.

5. The camera assembly as set forth in claim wherein the inner gantry structure rotating means further includes:
   a large diameter toothed gear connected with one of the inner and outer races; and
   a motive power means for providing motive power to a means for engaging the toothed gear, the motive power means being operatively connected with the other bearing race.

6. The camera assembly as set forth in claim 5 wherein the toothed gear is connected with the inner race, the motive power means includes a motor which is mounted to the outer gantry structure and a small diameter toothed gear driven by the motor whose teeth intermesh with teeth of the large diameter gear.

7. A gamma camera assembly comprising:
   a large diameter bearing having an inner race and an outer race supported by an outer gantry structure, the inner and outer races defining a bearing plane which intersect at least one of the inner and outer races in a ring of points;
   a rotating means for selectively rotating the inner race relative to the outer race;
   a first detector head;
   a means for mounting a central portion of the first detector head within the inner race for rotation about a first axis which first axis lies in the bearing plane, the large diameter bearing extending peripherally around the the detector head;
   a first detector head angular position adjusting means for selectively rotating the first head around the first axis;
   a first head translating means for selectively translating the first detector head and the first detector head angular position adjusting means such that the first axis moves along the bearing plane.

8. The camera assembly as set forth in claim 7 wherein the inner gantry structure rotating means further includes:
   a large diameter toothed gear connected with one of the inner and outer races; and
   a motive power means for providing motive power to a means for engaging the toothed gear, the motive power means being operatively connected with the other bearing race.

9. The camera assembly as set forth in claim 8 wherein the toothed gear is connected with the inner race and the motive power means is a motor which is mounted to the outer gantry structure.

10. A gamma camera assembly comprising:
    a patient table supported at both ends for selectively supporting a patient along a longitudinal axis;
    an outer gantry structure mounted at least below the table;
    an outer gantry structure moving means for selectively moving the outer gantry structure parallel to the patient table;
    an inner gantry structure surrounding the patient table;
    a bearing parallel within a bearing plane and between the inner and outer gantry structures for rotatably mounting the inner gantry structure on the outer gantry structure;
    first and second detector heads mounted to the inner gantry structure along first and second axes, respectively, for rotation thereabout, the first and second axes being disposed parallel to each other in the bearing plane, the first and second camera heads further being mounted to the inner gantry structure for selective movement along the bearing plane toward and away from the patient table.

11. The camera assembly as set forth in claim 10 further including a large diameter bearing having an inner race connected with the inner gantry structure and an outer race connected with the outer gantry structure, the large diameter bearing extending peripherally around the inner gantry structure and the detector heads.

12. The camera assembly as set forth in claim 11 wherein the inner gantry structure rotating means further includes:
   a large diameter toothed gear connected with one of the inner and outer races; and
   a motive power means for providing motive power to a means for engaging the toothed gear, the motive power means being operatively connected with the other bearing race.

13. The camera assembly as set forth in claim 12 wherein the toothed gear is connected with the inner race, the motive power means is a motor which is mounted in the outer gantry structure and a small diameter toothed gear whose teeth intermesh with teeth of the large diameter gear.

14. A gamma camera assembly comprising:
   a patient table supported at both ends;
   an outer gantry structure movably mounted at least below the patient table for movement parallel to a longitudinal axis;
   a large diameter bearing lying in and defining a bearing plane transverse to the longitudinal axis, the bearing having an outer race stationarily mounted to the outer gantry structure;
   an inner gantry structure mounted to an inner race of the large diameter bearing;
   a means for mounting a first detector head to the inner race including a detector head angular position adjusting means for rotating the detector head about a first axis disposed within the bearing plane, and a translating means for moving a center portion of the head along the inner gantry structure in the bearing plane toward and away from the longitudinal axis.

15. The camera assembly as set forth in claim 14 further including:
   a large diameter gear connected with one of the inner and outer races;
   a motor operatively connected with the other bearing race; and
   a driven gear driven by the motor and interacting with the large diameter gear to cause the inner race to rotate relative to the outer race.

16. The camera assembly as set forth in claim 14 further including:
   a second detector head mounted to the inner gantry structure;
   a second detector head angular position of the second head relative to a second axis extending through the inner gantry structure and in a plane perpendicular to the longitudinal axis;
   a second head translating means for selectively translating the second head toward and away from the longitudinal axis;
   and means for selectively rotating the inner gantry structure relative to the outer gantry structure.

17. A gamma camera assembly comprising:
   a patient table supported at both ends;
   an outer gantry structure movably mounted at least below the patient table for movement parallel to a longitudinal axis;
   a large diameter bearing having an outer race stationarily mounted to the outer gantry structure;
   an inner gantry structure mounted to an inner race of the large diameter bearing, the inner gantry structure defining a central aperture for selectively receiving the patient table;
   a first detector head mounted to the inner gantry structure and disposed in the inner gantry central aperture;
   a second detector head mounted to the inner gantry structure and disposed in the inner gantry central aperture;
   a first head angular position adjusting means for rotating the first detector head about a first axis extending through the first detector head and the inner gantry in a plane defined by the inner race, the first head angular position adjusting means rotating the first head at least between a parallel orientation in which its face is parallel to the longitudinal axis and a transverse orientation in which its face is transverse to the longitudinal axis;
   a second head angular position adjusting means for rotating the second detector head about a second axis extending through the second detector head and the inner gantry in the plane define by the inner race, the second head angular position adjusting means rotating the second head at least between a parallel orientation in which its face is parallel to the longitudinal axis and a transverse orientation in which its face is transverse to the longitudinal axis;
   the central aperture having a dimension sufficient to accommodate the first and second detector heads both in the transverse orientation to detect gamma radiation traveling parallel to the longitudinal axis;
   a first head translating means for translating the first head along the plane defined by the inner race toward and away from the longitudinal axis;
   a second head translating means for translating the second head along the plane defined by the inner race toward and away from the longitudinal axis.

* * * * *